May 21, 1974 W. A. WARRINER Plant Pat. 3,555
ROSE PLANT
Filed Nov. 7, 1972
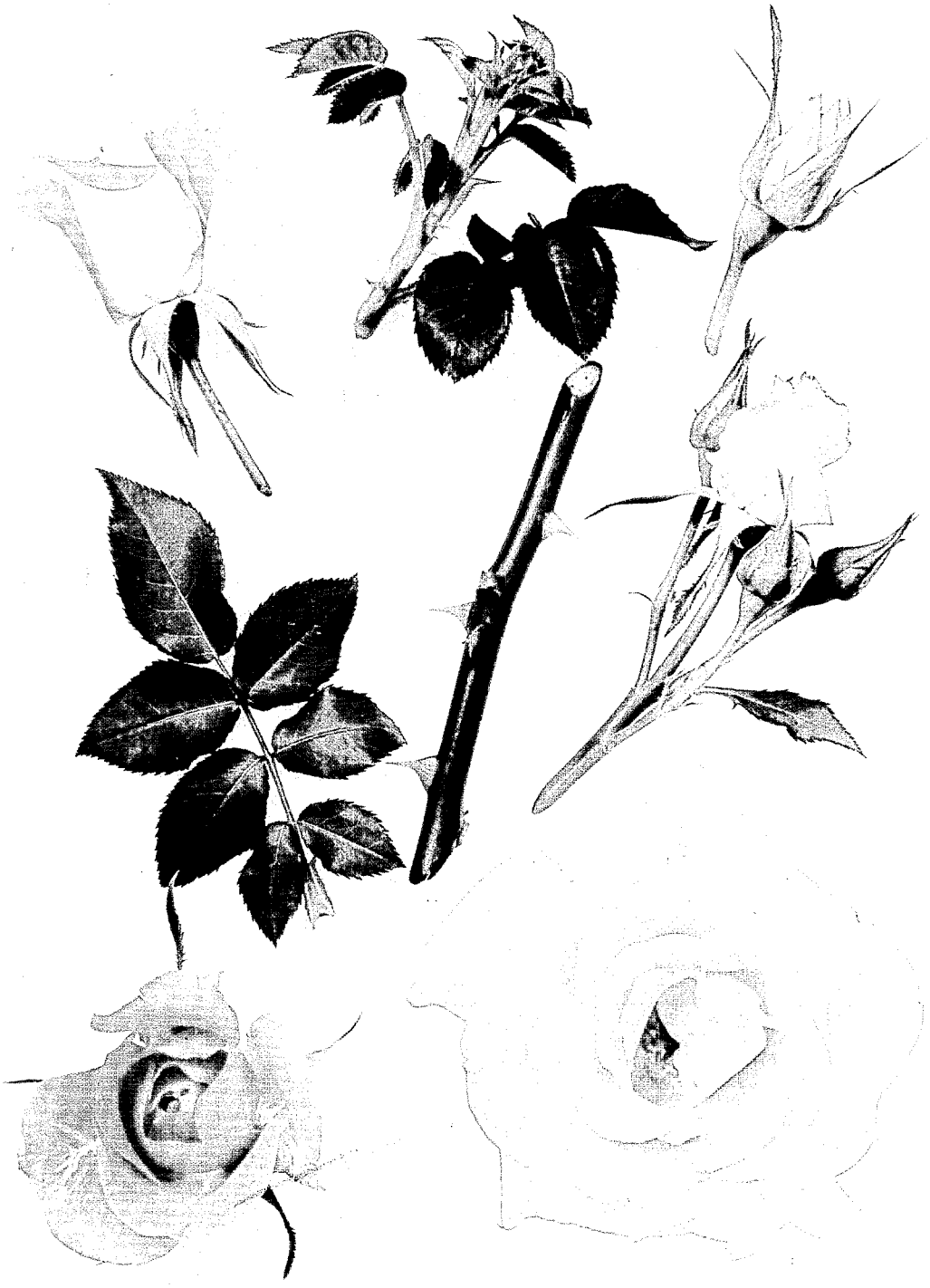

United States Patent Office

Plant Pat. 3,555
Patented May 21, 1974

3,555
ROSE PLANT

William A. Warriner, Tustin, Calif., assignor to Jackson & Perkins Company, Medford, Oreg.

Filed Nov. 7, 1972, Ser. No. 304,383
Int. Cl. A01h 5/00
U.S. Cl. Plt.—22 1 Claim This present invention relates to a new and distinct variety of rose plant of the floribunda class which was originated by me by crossing the variety Bridal Pink, U.S. Pl. Pat. 2,851, with pollen from an unnamed seedling variety.

The primary objective of this breeding was to produce a new rose variety of the floribunda class, comparable to Bridal Pink in plant habit but with much larger flowers. This objective was substantially achieved along with other desirable improvements as evidenced by the following unique combinations of characteristics which are outstanding in the new variety and which distinguish it from its parents as well as from all other varieties of which I am aware:

1. A vigorous but compact plant with a wide spreading habit of growth.
2. Large semidouble flowers borne mostly in clusters on relatively short stems.
3. Flower color of Rose Madder with the reverse of the petals being lighter shade of Rose Madder giving a pronounced bicolar effect in the half-open stage.

Asexual reproduction of this new variety by budding, as performed at Wasco, California, shows that the foregoing characteristics and distinctions come true to form and are established and transmitted through succeeding propagations.

The accompany drawing shows typical specimens of the vegetative growth and flowers of this new variety in different stages of development, depicted in color as nearly true as it is reasonably possible to make the same in a color illustration of this character.

The following is a detailed description of my new rose variety with color terminology in accordance with *Wilson's Horticultural Color Chart,* except where ordinary dictionary significance of color is indicated.

Parentage: Seedling.
*Seed parent*—Bridal Pink.
*Pollen parent*—Unnamed seedling.
Classification:
*Botanic*—Rosa hybrid.
*Commercial*—Floribunda.

FLOWER

Observations were made at Irvine, California in August in the afternoon in the garden.

Blooming habit: Recurrent—continuous.
Bud:
*Size*—¾ inch-one inch when petals start to unfurl.
*Form*—Pointed, broad base.
*Color*—When sepals first divide slightly darker than Rose Opal (022). When half blown; inside of petals Rose Madder (23). Reverse of petals: Outside petals Rose Madder (23/2) overlaid where exposed to sun with Rose Madder (23). Inner petals Rose Madder (23/3) or slightly lighter.
*Sepals*—Color: Outer surface—base and midrib area Pod green (061); outer edges are near Scheeles green (860/3). There are numerous small stipitate glands on outer surface. Inner surface—Lightly tomentose. Basically same color as outer surface.

Three appendaged sepals lightly appendaged. Two unappendaged sepals smooth edged.
*Receptacle*—Color: Near Scheels Green (860/2). Shape: Funnel. Size: Small. Surface: Slightly glandular.
*Penduncle*—Length: Short. Surface: Long stipitate glands. Color: Light green. Strength: Stiff, erect.
*Opening*—Petals fold out without curling back.
Bloom:
*Size*—Very large. Average size when fully expanded 3½–4½ inches.
*Borne*—Singly and in flat clusters.
*Stems*—Medium and short, strong.
*Form*—When first open, flat. Permanence—retains its form until the end.
*Petalage*—Number of petals under normal conditions 16–20.
*Color*—Center of flower: Upper side of petals Rose Madder (23). Reverse side of petals Rose Madder (23/3) or slightly lighter. Outer petals: Upper side of petals Rose Madder (23/2) with occasional whitish or pale pink variegation. Reverse of petals: Nearly white, but with pinkish cast. Base of petals: Triangular area 5/16 inch on each side is near white darkening to Primose Yellow (601/1) at point of attachment. General tonality from a distance Rose Madder (23). No variegations.
*Discoloration*—General tonality at end of first day Rose Madder (23). By third day slightly lightened to Rose Madder (23/1).
*Fragrance*—Slight.
Petals:
*Texture*—Thick.
*Surface*—Inside—satiny. Reverse—satiny.
*Shape*—Round.
*Form*—Edges slightly undulated.
*Arrangement*—Loosely imbricated.
*Petaloids in center*—Few.
*Persistence*—Drop off cleanly.
*Lastingness*—On the plant—long. As cut flower—long.
Reproductive parts:
*Stamens, anthers*—Large. Color—yellow. Arrangement—regular around styles.
*Stamens, filaments (threads)*—Short. Color—Yellow.
*Styles*—Loosely separated, of uneven lengths.
*Ovaries*—All enclosed in calyx.
*Stigmas*—Color—white .

PLANT

Form: Bush.
Growth: Vigorous, upright, compact.
Foliage: Number of leaflets on normal mid-stem leaves. 5, occasionally 7.
*Size*—Large.
*Quantity*—Normal.
*Color*—New foliage: Slightly lighter than Garnet Brown (00918/3).—Old foliage: Near Parsley green (00962/1), upper side near Willow green (000862).
Leaflets:
*Shape*—Oval pointed.
*Texture*—Upper side leathery. Under side smooth. Ribs and veins, ordinary.
*Edge*—Serrated.
*Serration*—Single, small.
*Petiole (rachis)*—Color—green. Underside—prickles and stipitate glands.

*Stipules*—Long, slightly serrated.

*Disease resistance*—Resistant to mildew under normal growing conditions at Irvine, California.

Wood:

*New wood*—Color—light green. Bark smooth.

*Old wood*—Color—green. Bark—smooth.

Prickles:

*Quantity*—On main stalks—ordinary. On laterals—ordinary.

*Form*—Oval, long, hooked slightly downward.

*Color*—When young—green.

*Position*—Irregular.

Small prickles:

*Quantity*—On main stalks—few. On laterals—few.

*Color*—Green.

I claim:

1. A new and distinct variety of rose plant of the floribunda class, substantially as herein shown and described, characterized particularly as to novelty by the unique combination of its compact, spreading plant, large semidouble Rose Madder flowers borne usually in clusters.

No references cited.

ROBERT E. BAGWILL, Primary Examiner